(12) United States Patent
Morice

(10) Patent No.: US 6,623,767 B1
(45) Date of Patent: Sep. 23, 2003

(54) MIXTURE CONTAINING HONEY, AT LEAST ONE ESSENTIAL OIL AND/OR AT LEAST ONE ESSENTIAL OIL DERIVATIVE

(76) Inventor: André Morice, 6, av., Anatole (FR)

(*) Notice: Subject to any disclaimer, the term of this patent is extended or adjusted under 35 U.S.C. 154(b) by 0 days.

(21) Appl. No.: 09/600,426

(22) PCT Filed: Jan. 6, 1999

(86) PCT No.: PCT/FR99/00010

§ 371 (c)(1),
(2), (4) Date: Jul. 13, 2000

(87) PCT Pub. No.: WO99/36052

PCT Pub. Date: Jul. 22, 1999

(30) Foreign Application Priority Data

Jan. 16, 1998 (FR) .............................. 98 00451

(51) Int. Cl.⁷ ................................. A61K 7/48
(52) U.S. Cl. ........................... 424/745; 424/47; 424/58; 424/64; 424/65; 424/69; 424/70.1; 424/401; 424/427; 424/433; 424/451; 424/464; 424/195.1
(58) Field of Search .............................. 424/401, 195.1, 424/70.1, 433, 427, 464, 451, 47, 64, 65, 69, 58, 745, 746

(56) References Cited

FOREIGN PATENT DOCUMENTS

FR          7727627           6/1996
WO          WO 98/40086    *  9/1998

OTHER PUBLICATIONS

RU abstract 2001944(10/93).*
ES abstract 2039180(4/94).*
SU abstract 538020(2/77).*
International Search Report from PCT/FR 99/00010 filed Jan. 6, 1999.
Base de Donnés "Chemical Abstracts" (Serveur: STN); abrégé 103: 27 321, Columbus, OH: & RO 82 337 B (Intreprindera Pentru Omogenizarea Mierii Si Productie Alimentara) Sep. 30, 1983 XP002097019.
Base de Donnés "Chemical Abstracts" (Serveur: STN); abrégé 126: 18 147, Colombus, OH; & LI 3104 B (V. seminiene et al.) Nov. 25, 1994 XP002097020.
Base de Donnés "Chemical Abstracts" (Serveur: STN); abrégé 103: 177 287, Colombus, OH; & HU 35 165 0 (J. Mathe et al.) Jun. 28, 1985 XP002097021.

* cited by examiner

*Primary Examiner*—Jyothsan Venkat
(74) *Attorney, Agent, or Firm*—Wolf, Greenfield & Sacks, PC

(57) ABSTRACT

The invention relates to a formulation comprising honey, at least one essential oil and/or at least on essential oil derivative. It also relates to the different uses of said formulation in the pharmaceutical, cosmetic and food industries.

11 Claims, No Drawings

MIXTURE CONTAINING HONEY, AT LEAST ONE ESSENTIAL OIL AND/OR AT LEAST ONE ESSENTIAL OIL DERIVATIVE

This application is 371 of PCT/FR99/00010 filed on Jan. 6, 1999.

The present invention relates to a formulation comprising honey.

Honey, known world-wide for its diverse origins, is already used, alone, for its cell and/or tissue regenerating properties.

Honey has the disadvantage of comprising different germs of a quantity according to its origin. Consequently, although it also offers interesting nutritive and gustatory characteristics, honey cannot be used in medical applications since it does represent a sterile medium.

In addition, essential oils are already used in the perfume and food industries for their olfactory and/or gustatory properties.

Also, there is a need for a sterile formulation, with interesting nutritive and gustatory characteristics, offering risk-free use for the human body and/or for animals for therapeutic purposes and/or in the cosmetic and/or food industry.

The present invention relates to a formulation comprising honey, characterised in that it comprises 1 to 5% by weight of at least one essential oil and/or at least one essential oil derivative selected from cloves, savory or oregano, with reference to the total weight of the formulation.

The formulation according to the invention offers the advantage of, firstly, eliminating the pathogenic or non-pathogenic germs present in honey and, secondly, can provide a sterile medium, capable of containing in its internal surface and/or harvesting on its surface, other chemical constituents and/or molecules, for therapeutic purposes and/or in the cosmetic and/or food industry. The presence of at least one essential oil and/or one essential oil derivative eliminates the germs potentially present in the honey. The concentration of chemical constituents added to the sterile medium depends on their type, the body's tolerance limit for each ingestion or cutaneous application and the physical structure of the chemical constituent.

This sterile medium also offers the advantage of having a sweet, pleasant taste, thus facilitating its ingestion by very young children and/or infants.

The formulation also offers the advantage of using honey, which an inexpensive natural product, as its main constituent. Honey, produced by bees and harvested easily in beehives, is free of exogenic substances, such as insecticides.

In addition, so that it can be used in the formulation according to the invention, the honey, when harvested, must not be subjected to any treatment, such as heating, which is often applied by beekeepers to make it easier to remove from the beehive.

The invention also relates to the use of a formulation comprising honey, at least one essential oil and/or at least one essential oil derivative as an antibacterial agent.

Thirdly, the invention relates to the use of a formulation comprising honey, at least one essential oil and/or at least one essential oil derivative for the production of a medicinal product intended to treat viral infections.

Fourthly, the invention relates to the use of a formulation comprising honey, at least one essential oil and/or at least one essential oil derivative for the production of a medicinal product intended to treat mycotic infections.

In the therapeutic field, the conditions for which the formulation can be used include, but not exhaustively, ENT infections, such as colds, influenza, tonsillitis, sinusitis, pneumological infections such as chronic bronchitis, gynaecological conditions such as menopause, hot flushes and gastro-enterological conditions such as constipation and diarrhoea.

In dermatology, the formulation may be used for chilblains, warts, burns, sunburn, acne and cellulite.

The invention also relates to the use of a formulation comprising honey, at least one essential oil and/or at least one essential oil derivative for the production of a medicinal product intended for cell and/or tissue regeneration.

Finally, the invention also relates to the use of a formulation comprising honey, at least one essential oil and/or at least one essential oil derivative as an excipient, food medium or cosmetic medium.

In the field of cosmetics, the formulation can particularly be used in skin treatment and/or care products such as moisturising, anti-wrinkle and slimming creams, in hair cleaning and/or care products such as shampoos, in soaps, in dental and mouth care products such as toothpaste and in hydrotherapy products for baths.

Honey is essentially composed of 20% water, 38% levulose, 31% glucose, 1.3% sucrose, 8.37% acid compounds (with an overall pH of 3.91), 0.83% proteins and 0.5% mineral salts.

The essential oil may be selected from natural or industrially synthesised essential oils and their derivatives.

To obtain the formulation according to the invention, the honey is firstly extracted from the honeycombs in the super hives, by centrifugation, at ambient temperature and pressure, and it is then mixed with at least one essential oil before it crystallises.

Preferably, the essential oil is selected from aromatic compounds and their esters, flavenoids, terpenes, phenols, alcohols and their esters, oxides, aliphatic and cyclic esters, sulphured aliphatic compounds, aldehydes, ketones, lactones, heterocycles comprising at least one oxygen atom, heterocycles comprising at least one nitrogen atom or at least one nitrogen and one sulphur atom, aromatic acids and their esters, aliphatic and cyclic esters, and their derivatives.

The quality of an essential oil is the result of the proportions of its constituents and the presence of specific substances, frequently in very low quantities.

Among natural essential oils, the formulation according to the invention may particularly comprise, eucalyptus radiata, ravensara aromatica, mint, lavender, thyme, savory, officinal sage, rosemary, cedarwood, clove, vetiver, geranium, bergamot, coriander, jasmine, rose and their derivatives.

Among the essential oils obtained by chemical synthesis, the formulation may comprise aliphatic and cyclic esters such as butyl acetate (apple), isoamyl acetate (banana), ethyl butyrate (pineapple), or aliphatic ketones such as diacetyl (constituent of butter) and their derivatives.

Among the non-cyclic terpenic alcohols, the formulation may comprise geraniol (rose), linalol (lily of the valley) and among the non-cyclic terpenic aldehydes, citral (neral+geranial) or citronelall and their derivatives may be used.

Among the sulphured aliphatic compounds, it is possible to use diallyldisulphide (garlic), cis and transpropenylpropyldisulphide (onion), or among the cyclic terpenic alcohols and their esters, bornyl acetate (pine needles) and their derivatives.

Among the cyclic terpenic ketones, it is possible to used menthone (mint), carvone (herbaceous odour), and their derivatives. The aromatic alcohols include benzyl alcohol, trans-cinnamic alcohol (hyacinth), 2-phenylethylene alcohol (rose) and their derivatives.

Among the aromatic aldehydes, it is possible to use trans-cinnamic aldehyde (cinnamon), benzaladehyde (bitter almond), phenylacetic acid (honey), isoamyl salicylate (clover), methyl anthranilate (orange blossom) and their derivatives.

Among the phenols and their esters and ethers, it is possible to use thymol (thyme), eugenol (clove), anethol (aniseed), and among the aldehyde phenols, vanillin (vanilla), and their derivatives.

In the family of heterocycles comprising at least one oxygen atom, it is possible to use coumarine (hay), ethyl-maltol (caramel), or among the heterocycles comprising at least one nitrogen atom or at least one nitrogen and sulphur atom, 2-isobutylthiazole (tomato) and their derivatives.

Preferably, the formulation comprises honey, at least one essential oil and/or one essential oil derivative selected from lemongrass, cloves, cinnamon, white thyme, red thyme, oregano and their derivatives.

Preferably, the formulation comprises honey and oregano.

The quantity of honey comprised is preferably between 0.5% and 25% by weight, preferably between 0.5% and 5% by weight, and more particularly 5% by weight with reference to the total weight of the formulation.

The quantity of essential oil present may be between 1% and 5% by weight, preferably between 1 and 2% by weight, and more particularly 1% by weight with reference to the total weight of the formulation.

More particularly, the formulation comprises 5% honey and 1% oregano.

The formulation; according to the invention may also comprise at least one additive selected from propolis, moisturising agents, perfumes, vitamins, trace elements, fats, surfactants, thickening agents, fillers, antioxidants, pigments, gelling agents, electrolytes, proteins, peptides, amino acids, carbohydrates, preservatives, colorants, water, alcohols, royal jelly, pollen and yeasts.

The trace elements include potassium, selenium, manganese, cobalt, zinc, copper, gold, silver and sulphur. The vitamins that can be incorporated in the formulation according to the invention include vitamins A, B1, B2, B5, B6, B8, B12, C, D3, PP.

Propolis is essentially composed of 50% to 55% resin and balm, 25 to 35% wax, 10% essential oils, 5% pollen and 5% various organic and mineral substances.

The additional presence of propolis in the formulation according to the invention stimulates the antibacterial, antimycotic and antiviral effect of said formulation.

According to a variant, the formulation may comprise 5% honey, 1% of at least one essential oil and/or at least one essential oil derivative and 1% propolis.

The proportion of additive comprised is preferably between 80% and 95% by weight, preferably between 85% and 88% by weight, and more particularly 90% by weight with reference to the total weight of the formulation.

The formulation according to the invention may be presented in the form of an oil in water or water in oil emulsion, an aqueous solution, a hydroalcoholic solution, aqueous gel, oily gel or a dispersion of vesicles.

The formulation according to the invention may be presented in different pharmaceutical forms, such as in the form of suppositories, tablets, capsules, ointment, ovules, solution, lotion, cream, milk, shampoo, soap, lipstick, makeup, foundation, powder, toothpaste, sun cream, deodorant, spray, dressings, syrup, eye drops, chewing gum, drinks, lollipops or ampoules.

The formulation according to the invention may consist of a food, cosmetic and/or dermatological formulation for the skin and/or mucosa.

The formulation according to the invention intended for use in the food industry may be presented in the form of anti-depressant, anti-stress, anti-ageing, dietary, fitness, aphrodisiac or anti-insomnia products.

In addition, said formulation may be intended to disinfect sanitary equipment such as intensive care rooms and rooms for contagious patients. The formulation may particularly come in the form of an aerosol combined with a deodorant or not.

The invention will now be described using the examples below, which are not restrictive.

The proportions are given as percentages by weight.

EXAMPLE 1

Product Intended to Treat Aphthous Ulcers

| | |
|---|---|
| Honey | 5% |
| Oregano hydrosol | 15% |
| Ravensara hydrosol | 15% |
| Myrtle hydrosol | 15% |
| Eucalyptus hydrosol | 50% |

This formulation, present in the form of a sprayable solution, makes it possible to eliminate the aphthous ulcers present on the mucosa inside the mouth completely within a few days, when applied twice-daily.

EXAMPLE 2

Product Intended to Treat Mycotic Infections

| | |
|---|---|
| Honey | 2% |
| Propolis | 10% |
| Clove | 0.4% |
| Savory | 0.3% |
| Oregano | 0.3% |
| Thyme | 0.2% |
| Lavender | 0.2% |
| Excipient (Lanolin) up to | 100 |

This formulation, present in ointment form, applied 3 times a day on skin lesions, enables the complete elimination of mycoses presence on the skin within a few days.

EXAMPLE 3

Product Intended to Treat Sinusitis

| | |
|---|---|
| Honey | 2% |
| White thyme | 1% |
| Mint | 1% |
| Eucalyptus | 1% |
| Pine | 1% |
| Propolis | 3% |
| Fragrance | |
| Excipient up to | 100 |

This formulation, present in inhalant lotion form, makes it possible to control and cure sinusitis within a few days.

EXAMPLE 4

Skin Wound Healing Product

A first formulation is applied on the wounds. Said formulation is as follows:

| | |
|---|---|
| Honey | 5% |
| Oregano | 1% |

-continued

| | |
|---|---|
| Propolis | 1% |
| Fragrance | |
| Excipient up to | 100 |

In the event of wound superinfection, a second formulation with the following formula is applied on the skin:

| | |
|---|---|
| Honey | 5% |
| Oregano | 0.9% |
| Savory | 0.2% |
| Sage | 0.3% |
| Propolis | 1% |
| Excipient up to | 100 |

Said formulations, present in the form of a dressing, enable the wounds to heal in a few days depending on the depth of said wounds.

EXAMPLE 5

Hair Care and Cleaning Product

| | |
|---|---|
| Honey | 2% |
| Sage | 0.5% |
| Eucalyptus | 0.5% |
| Brewer's yeast | 1% |
| Surfactant | 1% |
| Moisturising agent (glycerol) | 2% |
| Fragrance | |
| Water up to | 100 |

This formulation, present in the form of an antidandruff shampoo, makes it possible to eliminate the dandruff present on the skin within a few days.

EXAMPLE 6

Product Intended to Treat Infections Present on the Internal Walls of the Vagina

| | |
|---|---|
| Honey | 0.5% |
| Melaleuca | 0.5% |
| Propolis | 1% |
| Excipient up to | 100 |

This product, present in ovule form, enables the treatment of infections within a few days when taken daily.

The tables below show the efficacy of the antibacterial property of the formulation according to the invention, as a function of the type of essential oil or essential oil derivative used, when said formulation is placed in the presence of germs belonging to different genera.

TABLES

| | Honey + essential oils | | | | | | | |
|---|---|---|---|---|---|---|---|---|
| Germ | Clove | Common thyme | Oregano | Mountain savory | Officinal sage | Officinal rosemary | Rosemary verbenone | Lemon-grass |
| *Streptococcus A* | ++ | ++ | +++ | +++ | | | ++ | |
| *Streptococcus B* | + | + | +++ | ++ | | ++ | | +++ |
| *Staphylococcus Aureus* | ++ | +++ | +++ | ++ | +++ | +++ | ++ | ++ |
| *E. Coli* | ++ | I | +++ | +++ | + | O | +++ | |
| *Candida Albicans* | ++ | +++ | +++ | +++ | + | +++ | | |

| | Honey + essential oils | | | | |
|---|---|---|---|---|---|
| Germ | Peppermint | Tarragon | *Eucalyptus globulus* | Rose geranium | Lavender |
| *Streptococcus A* | + | | + | – | I |
| *Streptococcus B* | + | | + | | I |
| *Staphylococcus Aureus* | +++ | | ++ | – | I |
| *E. Coli* | + | | + | | O |
| *Candida Albicans* | I | +++ | + | +++ | ++ |

The number of crosses indicates the intensity of the efficacy of the formulation. The higher this number is, the greater the efficacy of the formulation. The letter "I" indicates a moderate efficacy and the letter "0" zero or near-zero efficacy. The symbol "–" indicates insufficient growth of the germs placed in culture in the presence of the formulation according to the invention.

The results in this table demonstrate that the formulation according to the invention comprising oregano shows a very marked efficacy in the presence of germs belonging to totally different genera.

Bacterial germs, mycoses and viruses are often present at the same time on and/or in the body. Consequently, this requires testing on the nature of said micro-organisms and of said structures, particularly through the use of different techniques used in molecular biology, such as "Hybrid capture" which consists of detecting a DNA virus versus an RNA virus, and/or techniques that detect oncogenic viruses versus non-oncogenic viruses.

What is claimed is:

1. Formulation comprising honey, wherein the formulation comprises 1 to 5% by weight of essential oils of cloves, savory and oregano, with reference to the total weight of the formulation.

2. Formulation according to claim 1, wherein the quantity of oil comprised is between 1 and 2% by weight with reference to the total weight of the formlulation.

3. Formulation according to claim 1, further comprising at least one additive selected from propolis, moisturising agents, perfumes, vitamins, trace elements, fats, surfactants, thickening agents, fillers, antioxidants, pigments, gelling agents, electrolytes, proteins, peptides, amino acids, carbohydrates, preservatives, colorants, water, alcohols, royal jelly, pollen and yeasts.

4. Formulation according to claim 3, characterised in that it comprises 5% honey, 1% by weight of essential oils of cloves, savory, and oregano, and 1% propolis.

5. Formulation according to claim 3, wherein the quantity of additive present is between 80% and 95% by weight with reference to the total weight of the formulation.

6. Formulation according to claim 1, wherein the formulation is presented in the form of an oil in water or water in oil emulsion, an aqueous solution, a hydroalcoholic solution, aqueous gel, oily gel or a dispersion of vesicles.

7. Formulation according to claim 1, wherein the formulation is presented in the form of suppositories, tablets, capsules, ointment, ovules, solution, lotion, cream, milk, shampoo, soap, lipstick, makeup, foundation, powder, toothpaste, sun cream, deodorant, spray, dressings, syrup; eye drops, chewing gum, drinks, lollipops or ampoules.

8. Formulation according to claim 1, wherein the formulation is a formulation for the skin and/or mucosa.

9. Formulation according to claim 1, wherein the formulation comprises a food formulation.

10. Formulation according to claim 1, wherein the formulation is a formulation for disinfecting sanitary equipment.

11. Formulation according to claim 5, wherein the quantity of additive present is between 85% and 88% by weight with reference to the total weight of the formulation.

\* \* \* \* \*

UNITED STATES PATENT AND TRADEMARK OFFICE
CERTIFICATE OF CORRECTION

PATENT NO.    : 6,623,767 B1
DATED         : September 23, 2003
INVENTOR(S)   : André Morice It is certified that error appears in the above-identified patent and that said Letters Patent is hereby corrected as shown below:

<u>Title page,</u>
Item [76], Inventors, should read:
-- [76] Inventor: André Morice, 6, avenue Anatole, Lorient (FR) --

Signed and Sealed this

Thirtieth Day of December, 2003

JAMES E. ROGAN
*Director of the United States Patent and Trademark Office*